United States Patent
Johnson et al.

(10) Patent No.: US 8,973,269 B2
(45) Date of Patent: *Mar. 10, 2015

(54) METHODS OF MAKING BIOMIMETIC DENTAL APPLIANCES

(75) Inventors: Ryan E. Johnson, St. Paul, MN (US); Naimul Karim, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 183 days.

This patent is subject to a terminal disclaimer.

(21) Appl. No.: 13/696,638

(22) PCT Filed: Jun. 7, 2011

(86) PCT No.: PCT/US2011/039358
§ 371 (c)(1), (2), (4) Date: Nov. 7, 2012

(87) PCT Pub. No.: WO2011/159520
PCT Pub. Date: Dec. 22, 2011

(65) Prior Publication Data
US 2013/0056892 A1 Mar. 7, 2013

Related U.S. Application Data

(60) Provisional application No. 61/355,883, filed on Jun. 17, 2010.

(51) Int. Cl.
*A61C 5/10* (2006.01)
*A61C 13/20* (2006.01)
(Continued)

(52) U.S. Cl.
CPC ......... *A61C 13/0004* (2013.01); *A61C 13/0013* (2013.01); *A61C 13/0022* (2013.01); *A61C 13/082* (2013.01); *A61C 13/083* (2013.01)

USPC ........... 29/896.1; 29/896.11; 264/16; 264/19; 700/118; 700/119

(58) Field of Classification Search
CPC ............... A61C 13/00; A61C 13/0003; A61C 13/0004; A61C 13/0006; A61C 13/0013; A61C 13/08
USPC .......... 29/896.1, 896.11; 264/16, 19; 700/119
See application file for complete search history.

(56) References Cited

U.S. PATENT DOCUMENTS 7,563,397 B2 * 7/2009 Schulman et al. ............... 264/16
7,605,817 B2 10/2009 Zhang
(Continued)

FOREIGN PATENT DOCUMENTS

WO WO 2009/070469 6/2009
WO WO 2010/074890 7/2010
(Continued)

*Primary Examiner* — Alexander P Taousakis
(74) *Attorney, Agent, or Firm* — Nicole J. Einerson

(57) ABSTRACT

A method of making a biometric dental appliance. A first article can be formed of a first material based on a first digital surface representation having a desired outer shape of the dental appliance. A portion of the first article can then be removed to form an outer layer of the dental appliance comprising a cavity dimensioned to accommodate an inner layer. A second article can be formed by filling the cavity of the first article with a second material. The second material can have at least one different structural and/or optical property than the first material. The second article can be further processed, as desired. For example, a desired inner shape can be formed in the second article. Such a desired inner shape can be based on a second digital surface representation of a dental object configured to receive the dental appliance.

15 Claims, 1 Drawing Sheet

(51) Int. Cl.
*A61C 13/00* (2006.01)
*A61C 13/08* (2006.01)
*A61C 13/083* (2006.01)

(56) References Cited

U.S. PATENT DOCUMENTS

| | | | |
|---|---|---|---|
| 7,698,014 B2 * | 4/2010 | Dunne et al. | 700/118 |
| 2004/0155975 A1 | 8/2004 | Hart | |
| 2006/0177792 A1 | 8/2006 | Touchstone | |
| 2007/0212667 A1 | 9/2007 | Jung | |
| 2009/0233258 A1 | 9/2009 | Luthardt | |
| 2009/0298017 A1 | 12/2009 | Boerjes | |
| 2010/0219546 A1 * | 9/2010 | Puttler et al. | 264/16 |
| 2010/0291505 A1 | 11/2010 | Rawley | |
| 2012/0251979 A1 * | 10/2012 | Karim et al. | 433/201.1 |
| 2012/0277899 A1 * | 11/2012 | Chun et al. | 700/118 |
| 2013/0081272 A1 * | 4/2013 | Johnson et al. | 29/896.1 |
| 2013/0277874 A1 * | 10/2013 | Johnson et al. | 264/16 |

FOREIGN PATENT DOCUMENTS

| | | |
|---|---|---|
| WO | WO 2010/093534 | 8/2010 |
| WO | WO 2011/159503 | 12/2011 |

* cited by examiner

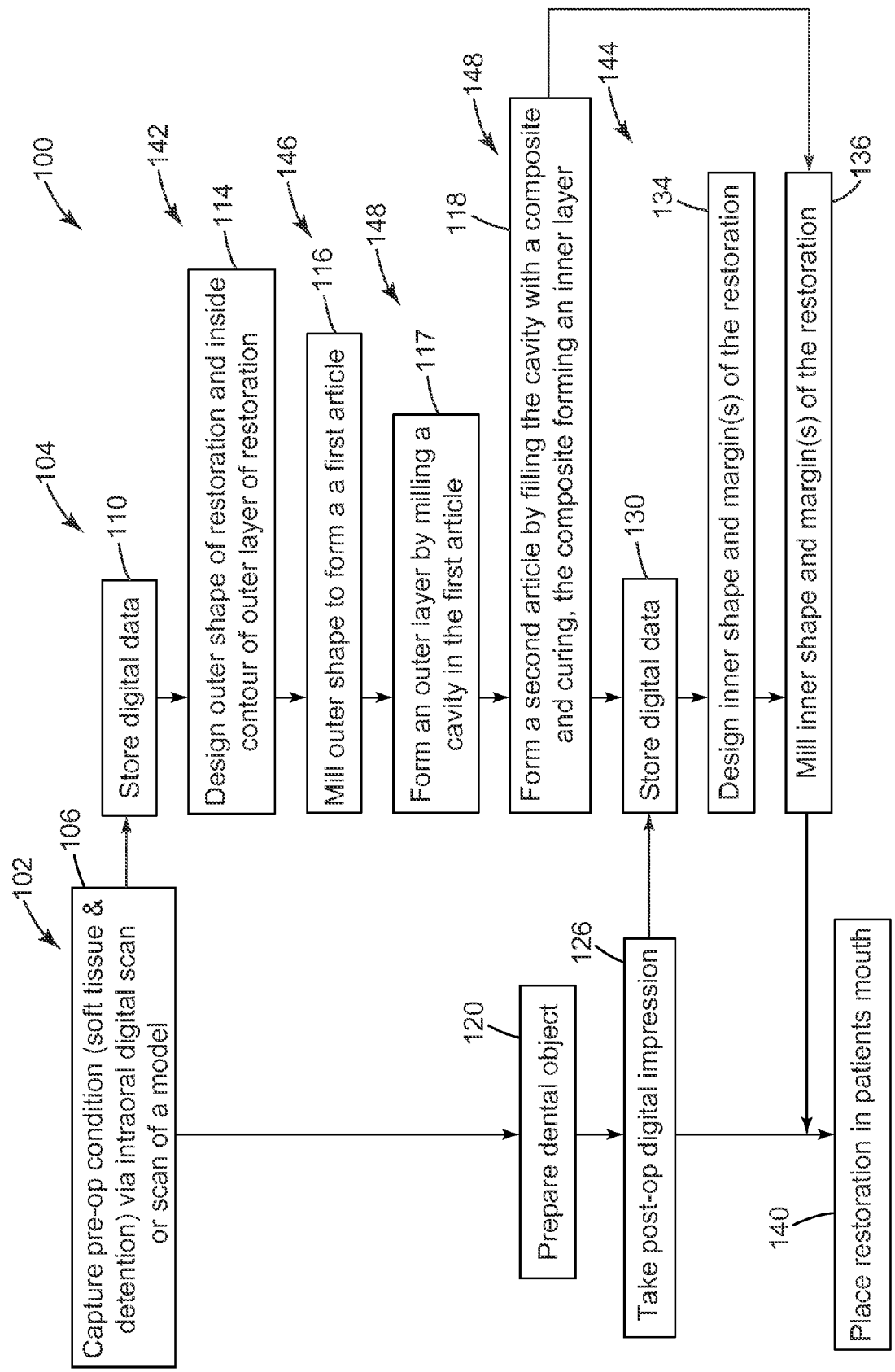

METHODS OF MAKING BIOMIMETIC DENTAL APPLIANCES

FIELD

The present disclosure is generally related to methods and workflows of making layered dental appliances, such as temporary or permanent dental restorations; particularly, to digital workflows for making biomimetic dental appliances; and more particularly, to at least partially chairside digital workflows for making layered, biomimetic dental appliances.

BACKGROUND

Digital dentistry generally includes using or creating one or more digital data files to prepare a dental appliance having a desired outer and/or inner shape and dimension. In some existing workflows, a desired outer shape of a final dental appliance can be determined; a tooth can be prepared (e.g., ground to a tooth stump); and a desired inner shape of the final dental appliance can be determined from the prepared tooth. A data file comprising the desired outer shape and the desired inner shape can then be used to create the final dental appliance having a desired outer and inner shape. For example, in some existing systems, the dental appliance can be formed by milling. However, milled dental appliances generally have a monolithic visual appearance, and uniform structural properties throughout, due to the corresponding, monolithic composition of dental mill blanks.

SUMMARY

The present disclosure generally relates to workflows that allow a desired outer shape (i.e., external surface, contours, etc.) of a dental appliance to be determined and created separately from that of a desired inner shape (i.e., internal surface, contours, etc., e.g., for accommodating a prepared tooth, an implant, an implant abutment, healing cap, or the like, or combinations thereof) of the same dental appliance; thus, generally separating the step for preparing the desired outer shape from the step for preparing the desired inner shape of a dental appliance.

Furthermore, the present disclosure generally relates to workflows that allow a desired outer layer of a dental appliance to be determined and created separately from that of a desired inner layer of the same dental appliance. The outer layer of the dental appliance can include a desired outer shape, as well as a desired inner shape or cavity. The inner layer of the dental appliance can also include a desired outer shape (e.g., that can match the inner shape of the outer layer, or that can be sized to accommodate cement or adhesive between the layers), and a desired inner shape (e.g., for accommodating a prepared tooth, an implant, an implant abutment, healing cap, or the like, or combinations thereof). For example, the inner layer can include a dental core or framework of a dental restoration. As a result, methods of the present disclosure can include separation of (e.g., temporally and/or spatially) the steps for designing and creating an outer layer of a dental appliance from steps for designing and creating an inner layer of the same dental appliance.

Some embodiments of the present disclosure provide a method of making a dental appliance. The method can include providing a first digital surface representation of a desired outer shape of a dental appliance, and forming a first article having the desired outer shape based on the first digital surface representation. The method can further include providing a dental object having an outer shape comprising the negative of a desired inner shape of the dental appliance; acquiring a second digital surface representation of the outer shape of the dental object; and subtractively forming the desired inner shape in the first article based on the second digital surface representation to form the dental appliance having the desired inner shape and the desired outer shape. At least one of providing a dental object and acquiring a second digital surface representation can occur during or after forming a first article. Furthermore, subtractively forming the desired inner shape can occur separately from and subsequently to forming a first article having the desired outer shape.

Some embodiments of the present disclosure provide a method of making a dental appliance. The method can include providing a first digital surface representation of a desired outer shape of a dental appliance, and forming a first article of a first material having the desired outer shape based on the first digital surface representation. The method can further include removing an inner portion of the first article to form an outer layer of the dental appliance comprising a cavity dimensioned to accommodate an inner layer, and forming a second article by filling the cavity of the first article with a second material adapted to form the inner layer. The method can further include providing a dental object having an outer shape comprising the negative of a desired inner shape of the dental appliance, and acquiring a second digital surface representation of the outer shape of the dental object. The method can further include subtractively forming the desired inner shape in the second article based on the second digital surface representation to form the dental appliance having the desired inner shape and the desired outer shape. In some embodiments of the method, at least one of providing a dental object and acquiring a second digital surface representation can occur during or after at least one of forming a first article, removing an inner portion of the first article, and forming a second article. Furthermore, in some embodiments of the method, subtractively forming the desired inner shape can occur separately from and subsequently to forming a first article of a first material having the desired outer shape.

Other features and aspects of the present disclosure will become apparent by consideration of the detailed description and accompanying drawings.

BRIEF DESCRIPTION OF THE DRAWINGS

FIG. 1 illustrates a flowchart of a method of making a layered, biomimetic dental appliance, according to one embodiment of the present disclosure.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "affixed," and "coupled" and variations thereof are used broadly and encompass both direct and indirect affixations and couplings. Further, "coupled" is not restricted to physical or mechanical connections or couplings. It is to be understood that other embodiments may be utilized, and structural or logical changes may be made without departing from the scope of the present disclosure. Furthermore, terms such as "front," "rear," "top," "bottom," "upper," "lower," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Some embodiments of the present disclosure generally relate to methods and workflows for making dental appliances, such as temporary or permanent dental restorations. Particularly, some embodiments generally relate to digital workflows for making dental appliances that do not require the final outer shape and the final inner shape of a dental appliance both be known prior to performing a first (e.g., outer) machining step. By not requiring that both the inner and outer shapes be known prior to any machining steps, machining a desired outer shape of the dental appliance can be performed separately from machining a desired inner shape. Further information and details regarding such methods can be found in co-pending U.S. Application No. 61/355,872, entitled, "METHODS OF MAKING DENTAL APPLIANCES," filed Jun. 17, 2010, which is incorporated herein by reference in its entirety.

The desired outer shape can be provided by an outer layer of the dental appliance, while the desired inner shape (which can be designed to accommodate a prepared tooth stump, an implant, an implant abutment, healing cap, or the like, or combinations thereof) can be provided by an inner layer of the dental appliance. Such dental objects, for example, can lack tooth-shaped supragingival exterior surfaces.

In some embodiments, as described in PCT Publication WO 2010/093534, the dental object (e.g., a healing cap) can be formed of a sufficiently malleable material such that the dental object can be customized in shape prior to hardening. In such embodiments, the inner shape of the dental appliance formed by processes of the present disclosure may not be so specifically controlled or designed, but rather can be designed to fit over a dental object that can conform to fit within the inner shape of the dental appliance. For example, the dental appliance can be pressed onto a malleable dental object, which can then be hardened.

The present disclosure also generally relates to methods and workflows for making dental appliances that do not require the outer layer and the inner layer of a dental appliance both be designed and known prior to creating the outer layer. By not requiring that both the outer layer and the inner layer be known prior to any forming (e.g., machining) steps, forming a desired outer layer of the dental appliance can be performed separately from forming a desired inner layer.

The outer layer and the inner layer, and any other layers, described herein that are formed by methods of the present disclosure generally include major or significant portions of the resulting dental appliance, and generally do not include bonding materials or bonding layers, such as cement or adhesives used, for example, to couple the dental appliance to a dental object (e.g., a tooth stump) and/or to couple layers of the dental appliance together. For example, in some embodiments, the outer layer, the inner layer, and any other layers described herein as forming a portion the dental appliance, generally form at least about 80% by volume (vol %) of the dental appliance, in some embodiments, at least about 90% by volume, and in some embodiments, at least about 95% by volume. Bonding materials, such as cement used to couple together layers of the dental appliance and/or to couple the dental appliance to a dental object, if employed, generally do not significantly contribute to the overall optical properties of the dental appliance.

Furthermore, some embodiments of the present disclosure generally relate to methods and workflows for making layered, biomimetic dental appliances, such that the outer layer and the inner layer will be different with respect to at least one structural or material property. As used herein, the term "biomimetic" generally refers to an object (e.g., a dental appliance) that is designed to imitate nature or biology in terms of visual aesthetics and/or function. Particularly, with respect to dental appliances, a "biomimetic" dental appliance can generally mimic the structural and/or material properties of a natural tooth, which generally has a harder enamel exterior and a softer dentin interior. For example, in some embodiments, the dental appliance can be layered and can preferably include a hard outer shell and a resilient internal structure, such that the internal structure can provide a sufficient amount of shock absorption that mimics a natural tooth. There may be situations in which a dental practitioner may choose to use a dental appliance that has a softer exterior and a harder interior. Therefore, in some embodiments, a biomimetic dental appliance can include two or more layers, and each layer can differ from another layer with respect to at least one structural and/or material property. Such structural and/or material (e.g., mechanical or physical) properties can include, but are not limited to, hardness, toughness, strength (e.g., strength under compression), impact resistance, elastic modulus, flexural modulus, abrasion resistance, polish retention, other suitable material properties, or combinations thereof. It can also be important in a biomimetic dental appliance that the outer layer and the inner layer (i.e., formed of a first material and a second material, respectively) have good interfacial bonding, for example, for structural integrity and sufficient biomimetics.

In some embodiments, at least a portion of the dental appliance can be formed of a glass-ceramic material and/or a polymeric (e.g., polymeric composite) material. In general, glass-ceramic materials are harder, have a higher elastic modulus, higher flexural modulus, higher abrasion resistance, and a higher polish retention than polymeric (e.g., polymeric composite) materials. In general, polymeric (e.g., polymeric composite) materials are tougher, and potentially more shock-absorbent and/or impact-resistant than glass-ceramic materials. Examples of suitable glass-ceramics and polymeric materials are described below.

In some embodiments, a biomimetic dental appliance can also be multi-chromatic and can be more natural-looking and/or aesthetically-pleasing. As used herein, the term "multi-chromatic" generally refers to an object (e.g., a dental appliance) that includes two or more layers, and wherein each layer is different from another layer with respect to at least one optical property. Such optical properties can include, but are not limited to, color or shade, transparency/translucency/opacity, reflectance, gloss or shine, refractive index, other suitable optical properties, or combinations thereof. Such optical properties can typically be visually distinguishable by the naked human eye. Methods and workflows for making multi-chromatic dental appliances are described in co-pending U.S. Application No. 61/355,876, entitled, "METHODS OF MAKING MULTI-CHROMATIC DENTAL APPLIANCES," filed on Jun. 17, 2010, which is incorporated herein by reference in its entirety.

By providing an inner layer and an outer layer of different material properties, a more natural-functioning dental appliance can be formed. For example, in the case of dental restorations, such as crowns and bridges, an outer layer can include a certain level of hardness, stiffness, and/or strength (e.g., under compression) to mimic an outer enamel shell, while the inner layer can include a certain level of toughness and/or resilience to mimic an internal dentin layer. In the case of bridges, each tooth unit on the bridge can include an interior cavity that is milled (i.e., to form an outer layer) and filled to form an inner layer of a different material property than the outer layer.

In addition, the inner layer and outer layer can have different optical properties, which can provide a more natural-looking and aesthetically-pleasing dental appliance. For example, in the case of dental restorations, such as crowns and bridges, an outer layer, in addition to being harder/stronger/stiffer, can include a certain level of translucency and can be shaded to mimic an enamel layer, while the inner layer, while being more resilient, can also include a certain level of opacity and can be shaded to mimic a dentin layer (e.g., the inner layer can be slightly darker in color than the outer layer). In the case of bridges, each tooth unit on the bridge can include an interior cavity that is milled (i.e., to form an outer layer) and filled to form an inner layer of a different optical property (e.g., shade) than the outer layer. In some embodiments, the inner layer can be provided by a composite material, such that internal shading of the dental appliance can be performed using a process similar to that for filling cavities in natural teeth.

While the present disclosure may emphasize certain steps and certain types of dental articles, it will be understood that additional variations, adaptations, and combinations of the methods and systems below will be apparent to one of ordinary skill in the art. For example, there are a number of variants to computer-controlled milling that may be suitably employed. Similarly, various types of cured or partially-cured materials may be employed for various fabrication steps, and a number of three-dimensional scanning technologies are available that might be suitably adapted to obtaining three-dimensional scans for the uses described herein. All such variations, adaptations, and combinations are intended to fall within the scope of this disclosure.

The methods of the present disclosure will generally be described as forming a two-layer dental appliance, including an outer layer and an inner layer. However, it should be understood that as many layers as necessary can be formed according to the techniques described herein, and the description of two layers is used only for simplicity and clarity. The phrases "outer layer" and "inner layer" can be used to describe an "outermost layer" and an "innermost layer," and as many intermediate layers as necessary can be formed between the outermost layer and the innermost layer, following the methods and workflows described herein.

The phrase "dental article" is to be understood as an article which can and is to be used in the dental or orthodontic area including dental laboratories, and can be used to described even intermediates in a dental workflow process.

The phrase "dental appliance" generally refers to any dental or orthodontic appliance or restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrases "mill block," "block," "blank," "mill blank," and "dental mill blank" generally refer to a solid block of material from which a desired product (e.g., a dental restoration) can be machined, and is not limited to the type of machining that will be used, even if referred to as a "mill" block. A mill block may have a size of about 10 mm to about 30 mm in two dimensions, for example may have a diameter in that range, and may be of a certain length in a third dimension. A mill block for making a single crown may have a length of about 15 mm to about 30 mm, and a blank for making bridges may have a length of about 40 mm to about 80 mm. In some embodiments, a mill block used for making a single crown can have a diameter of about 24 mm and a length of about 19 mm. In some embodiments, a mill block used for making bridges can have a diameter of about 24 mm and a length of about 58 mm. In general, mill blanks are attached to a mandrel that fits into a milling machine. The term mandrel can also be understood to include other methods of mounting mill blanks, such as frames (e.g., a Lava frame available from 3M ESPE, Seefeld, Germany).

The term "machining" generally refers to shaping a material by a machine, and can be employed to create custom-fit dental appliances having a desired shape and morphology. Machining can include, but is not limited to, one or more of milling, grinding, cutting, carving, abrading, polishing, controlled vaporization, electronic discharge milling (EDM), cutting by water jet or laser, any other suitable method of cutting, removing, shaping or carving material, or a combination thereof. In some cases, milling can be faster and more cost-effective than grinding. The term "mill block" or "blank" can be used to describe a starting material that will be machined to form a dental appliance.

While machining a mill block using a hand-held tool or instrument is possible, preferably the prosthetic is milled by machine, including computer controlled milling equipment. Some embodiments of the present disclosure employs a CAD/CAM device capable of milling a block, such as the Cerec System (available from Sirona Dental Systems, Germany). By using a CAD/CAM machining (e.g., milling) device, the dental appliance can be fabricated efficiently and with precision. During machining, the contact area may be dry, or it may be flushed with a lubricant. Alternatively, it may be flushed with an air or gas stream. Suitable lubricants can include water, oil, glycerin, ethylene glycols, silicones, or combinations thereof. After machining, some degree of finishing, polishing and adjustment may be necessary to obtain a custom fit and/or aesthetic appearance.

The phrase "dental restoration" is generally used to refer to any restoration that can be used in the dental field, including, but not limited to, crowns, partial crowns, inlays, onlays, abutments, bridges (e.g., including 2-unit, 3-unit, 4-unit, 5-unit or 6-unit bridges), implants, healing caps, other suitable dental articles, and combinations thereof. The dental restoration can include a three-dimensional inner and outer surface including convex and concave structures. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm. In some embodiments, the dental restoration can comprise or consist essentially of a glass ceramic, a polymeric composite, or a combination thereof.

Methods of the present disclosure can generally include the following steps:
  (i) providing a first digital surface representation corresponding to a desired outer shape of a dental appliance;
  (ii) forming a first article of a first material having the desired outer shape that corresponds to the first digital surface representation;

(iii) removing an inner portion of the first article to form an outer layer of the dental appliance comprising a cavity dimensioned to accommodate an inner layer;

(iv) forming a second article by filling the cavity of the first article with a second material adapted to form the inner layer, the second article still including the desired outer layer and outer shape;

(v) providing a dental object having an outer shape comprising the negative of a desired inner shape of the dental appliance;

(vi) acquiring a second digital surface representation of the outer shape of the dental object; and (vii) subtractively forming (e.g., machining) the desired inner shape in the second article (e.g., in the inner layer of the second article) that corresponds to the second digital surface representation to form the dental appliance having the desired inner shape and the desired outer shape;

wherein at least one of steps (v) and (vi) can occur during or after any or all of steps (ii)-(iv), such that any or all of steps (ii)-(iv) (or even steps (i)-(iv)) can occur at least partially simultaneously with steps (v) and (vi); and wherein step (vii) occurs separately from and subsequently to steps (ii)-(iv).

In some embodiments, following the above steps (i)-(vii), the method can further include step (viii) in which the dental appliance is placed in the patient's mouth.

In some embodiments, all of the above steps (i)-(viii) can be performed "chairside," such that all of the steps occur during one patient appointment or visit, e.g., at a dentist's office. In some embodiments, at least some of the above steps (e.g., any or all of steps (i)-(iv)) can be performed prior to (and potentially at a different location from) the appointment in which the remaining steps occur. The phrase "dentist's office" is used herein to generally refer to a facility or venue (e.g., a healthcare facility, a clinic, a dentist's office, an orthodontist's office, or the like) in which a patient would be prepared to receive, and would receive, a dental appliance. As such, the phrase "dentist's office" is not intended to be overly limiting, and is used only for simplicity.

The methods of the present disclosure can be "mold-free" methods, in which the outer shape and inner shape can be formed directly from the first digital surface representation and the second digital surface representation, respectively, without first creating an intermediate or temporary structure, such as a mold.

Step (i): Providing a First Digital Surface Representation

In some embodiments, step (i) above, "providing a first digital surface representation corresponding to a desired outer shape," can include performing a digital data capture of a patient's anatomy via digital impressioning (e.g., optically scanning a patient's mouth, which is described in greater detail below), or computed tomography (CT) (or computer-aided tomography (CAT)). Alternatively, the data capture can indirectly capture the patient's anatomy by performing a digital data capture of a plaster model (e.g., of the patient's mouth) or of a dental impression (e.g., of the patient's mouth), rather than directly capturing the patient's anatomy. In the case of using a dental impression, the digital data capture can be inverted from a negative volume to a positive volume. As a result, the first digital surface representation can be obtained prior to the time or date at which the remaining steps occur. Alternatively, or additionally, at least a portion of the first digital surface representation can be provided by a series of tooth libraries, or databases, that can be adaptive to replicate a portion or all of a tooth, which may be necessary for a severely worn, fractured, or implant usage, altogether absent tooth.

Performing a digital data capture can also be referred to as performing a digital workflow. Such a digital workflow can include optically scanning an object (e.g., a patient's mouth, a plaster model, an impression, etc.) to develop one or more digital data files (e.g., which can form, or be consolidated to form, a digital surface representation) representative of the desired dental appliance. Particularly, in step (i), the digital workflow is used to develop various images for the desired outer shape of the desired dental appliance. Such scanning can be performed using an optical scanner that is coupled to a computer-aided design (CAD) system that functions in conjunction with a computer-integrated manufacturing (CIM) system. Such a CIM system is available, for example, under the trade designation LAVA™ from 3M ESPE AG (Seefeld, Germany). Such optical scanning processes will now be described in greater detail.

In some embodiments, the first digital surface representation can be provided by a tooth library; can be known (e.g., stored in a library or in a patient's file history) from a previous digital data capture; the digital data capture can be taken at the same visit in which the patient will receive the finished dental appliance; or a combination thereof.

An example of a three-dimensional scanning system that may be employed in executing methods of the present disclosure is described in PCT Publication No. WO2009/070469, entitled "Fabrication of Dental Articles using Digitally-controlled Reductive and Digitally-controlled Additive Processes," filed on Nov. 18, 2008, which is incorporated herein by reference in its entirety.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional surface representation," "digital surface representation," "three-dimensional surface map," "three-dimensional model," and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

Acquiring digital surface representation of intraoral structures is generally known. For example, U.S. Pat. No. 7,698,014; incorporated herein by reference, describes a method of acquiring a digital surface representation of one or more intraoral surfaces and processing the digital surface representation to obtain a three-dimensional model. Such a method can be employed in the methods of the present disclosure to obtain a first digital surface representation.

As described in U.S. Pat. No. 7,698,014, FIG. 2 shows an image capture system 200 that may include a scanner 202 that captures images from a surface 206 of a subject 204, such as a dental patient, and forwards the images to a computer 208, which may include a display 210 and one or more user input devices such as a mouse 212 or a keyboard 214. The scanner 202 may also include an input or output device 216 such as a control input (e.g., button, touchpad, thumbwheel, etc.) or a display (e.g., LCD or LED display) to provide status information.

The scanner 202 may include any camera or camera system suitable for capturing images from which a three-dimensional point cloud may be recovered. For example, the scanner 202 may employ a multi-aperture system as disclosed, for example, in US Patent Publication No. 2004/0155975 to Hart et al ("Hart"). While Hart discloses one multi-aperture system, it will be appreciated that any multi-aperture system suitable for reconstructing a three-dimensional point cloud from a number of two-dimensional images may similarly be employed in the methods of the present disclosure. In one multi-aperture embodiment, the scanner 202 may include a plurality of apertures including a center aperture positioned along a center optical axis of a lens and any associated imaging hardware. The scanner 202 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 202 may include suitable processing for deriving a three-dimensional point cloud from an image set or a number of image sets, or each two-dimensional image set may be transmitted to an external processor such as contained in the computer 208 described below. In other embodiments, the scanner 202 may employ structured light, laser scanning, direct ranging, or any other technology suitable for acquiring three-dimensional data, or two-dimensional data that can be resolved into three-dimensional data.

In one embodiment, the scanner 202 is a handheld, freely positionable probe having at least one user input device 216, such as a button, lever, dial, thumb wheel, switch, or the like, for user control of the image capture system 200 such as starting and stopping scans. In an embodiment, the scanner 202 may be shaped and sized for dental scanning More particularly, the scanner may be shaped and sized for intraoral scanning and data capture, such as by insertion into a mouth of an imaging subject and passing over an intraoral surface 206 at a suitable distance to acquire surface data from teeth, gums, and so forth. The scanner 202 may, through such a continuous acquisition process, capture a point cloud of surface data having sufficient spatial resolution and accuracy to prepare a dental model, either directly or through a variety of intermediate processing steps.

Although not shown in FIG. 2, it will be appreciated that a number of supplemental lighting systems may be employed during image capture. For example, environmental illumination may be enhanced with one or more spotlights illuminating the subject 204 to speed image acquisition and improve depth of field (or spatial resolution depth). The scanner 202 may also, or instead, include a strobe, flash, or other light source to supplement illumination of the subject 204 during image acquisition.

The computer 208 may be, for example, a personal computer or other processing device. In one embodiment, the computer 208 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 208 may vary according to the size of the subject 204, the speed of image acquisition, and the desired spatial resolution of three-dimensional points. The computer 208 may also include peripheral devices such as a keyboard 214, display 210, and mouse 212 for user interaction with the camera system 200. The display 210 may be a touch screen display capable of receiving user input through direct, physical interaction with the display 210.

Communications between the computer 208 and the scanner 202 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 202 to the computer 208 may be secured. The computer 208 may generate control signals to the scanner 202 which, in addition to image acquisition commands, may include conventional camera controls such as focus or zoom.

In an example of general operation of a three-dimensional image capture system 200, the scanner 202 may acquire two-dimensional image sets at a video rate while the scanner 202 is passed over a surface of the subject. The two-dimensional image sets may be forwarded to the computer 208 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 202. One useful example of such a technique is described in commonly-owned U.S. Pat. No. 7,605,817, incorporated herein by reference. However, it will be appreciated that this example is not limiting, and that the principles described herein may be applied to a wide range of three-dimensional image capture systems.

The display 210 may include any display suitable for video or other rate rendering at a level of detail corresponding to the acquired data. Suitable displays include cathode ray tube displays, liquid crystal displays, light emitting diode displays and the like. In some embodiments, the display may include a touch screen interface using, for example capacitive, resistive, or surface acoustic wave (also referred to as dispersive signal) touch screen technologies, or any other suitable technology for sensing physical interaction with the display 210.

The digital surface representation may be processed with one or more post-processing steps. This may include a variety of data enhancement processes, quality control processes, visual inspection, and so forth. Post-processing steps may be performed at a remote post-processing center or other computer facility capable of post-processing the imaging file, which may be, for example a dental laboratory. In some cases, this post-processing may be performed by the image capture system 200. Post-processing may involve any number of clean-up steps, including the filling of holes, removing of outliers, etc.

Data enhancement may include, for example, smoothing, truncation, extrapolation, interpolation, and any other suitable processes for improving the quality of the digital surface representation or improving its suitability for an intended purpose. In addition, spatial resolution may be enhanced using various post-processing techniques. Other enhancements may include modifications to the data, such as forming the digital surface representation into a closed surface by virtually providing a base for each arch, or otherwise preparing the digital surface representation for subsequent fabrication steps.

As a result, such an above-described digital workflow includes scanning to capture a three-dimensional representation of some or all of the dentition of a patient's intraoral surfaces, at least at the desired location, i.e. typically the tooth structures directly adjacent those that will come in contact with the dental appliance that will be placed in the patient's mouth. This can sometimes be referred to as capturing the "pre-op" condition, and can include capturing a representation of soft tissue as well as dentition.

As mentioned above, in some embodiments, at least a portion of a tooth may be missing or broken. In such cases, a library of tooth forms for each human tooth (e.g., the first molar) may be provided by software and used to form the first digital surface representation, or merged with any acquired digital data files to form the first digital surface representation.

Thus, the digital surface representations may be created by consolidating or merging various digital data files (e.g., including data files acquired by optically scanning and/or data files previously acquired and/or provided by tooth libraries), and the digital data files or the resulting digital surface representation can be transmitted to a rapid fabrication facility such as a dental laboratory, an in-house dental laboratory at a dentist's office, or any other facility with machinery to fabricate physical models from digital models. In yet another embodiment, the digital surface representations may be downloaded from an internet site.

Any suitable optical scanner that can perform the above-described optical scanning procedures can be employed in step (i) of the method. Two exemplary optical scanners include a Cerec System, available from Sirona Dental Systems (Germany), and an E4D Dentist Chairside CAD/CAM System, available from D4D Technologies (Richardson, Tex.).

Providing the first digital surface representation can also include some of the above-described steps that include consolidating various data files or images and/or designing the outer contours, i.e., the "digital surface representation" representative of the "outer shape" of the desired dental appliance. Such designing of the final desired outer shape can be performed by, or can be completed using input from, the dentist (or dental practitioner), for example, and can include at least some of the above-described processing, post-processing, and/or data enhancement steps. That is, such finalizing can include manipulating the digital surface representation using software tools to alter the shape, size, positioning, and/or relationship to adjacent and antagonist teeth, of all or a part of the dental appliance. Such manipulation can be performed by a dental practitioner (e.g., a dentist, a dental assistant, a dental lab technician, or other suitable dental practitioner). Alternatively, the digital surface representation formed by combining digital data files can be used without modification (which can be referred to as a "clone" in some software programs). In some embodiments, such finalizing or manipulation of the digital surface representation that is representative of the desired outer shape of the desired dental appliance can be considered to be a part of step (ii), "forming a first article having the desired outer shape."

The first digital surface representation can include information relating to the outer surface or outermost shape, as well as information regarding the inner cavity shape of the outer layer, such as thickness of the outer shape, any internal mammelon structure, or any other information relating to desired inner surfaces of the outer layer (or, said another way, the desired outer surfaces of the inner layer of the desired dental appliance). Generally, information relating to internal mammelon structure and/or optical properties can be input into the model manually when designing the desired outer layer, for example, by comparing color chips, using a color camera, choosing colors from libraries or databases, etc.

As a result, the step of providing a first digital surface representation can also include providing the above information regarding the desired outer layer (or, equivalently, the desired inner layer) as digital data files, and merging such digital data files with any data files regarding the desired outer shape to form the first digital surface representation. Such additional information relating to the color, shading, and/or translucency, as well as the depth of any such parameters, can be provided by one or more libraries, or a patient's file history.

Such specific design characteristics may be unique for each tooth. For example, a front incisor may be different from a rear molar. For a two-layer dental appliance, this design information can determine the thickness of the outer layer at each point on the dental appliance. For example, the outer layer of the dental appliance may be thicker near the occlusal surface than it is near the gingival margin.

Alternatively, the outer layer may simply be set (and the first digital surface representation adjusted accordingly) to a uniform thickness, such as 1 mm or 2 mm. Software, particularly CAD/CAM software associated with a fabrication tool, can allow a dental practitioner to select between uniform thickness of the outer layer, thickness information from a library or database, to use software tools to customize and design the thickness of the outer layer at various points on the dental appliance, or a combination thereof.

Step (ii): Forming a First Article of a First Material Having the Desired Outer Shape Step (ii) above, "forming a first article of a first material having the desired outer shape that corresponds to the first digital surface representation" can include transmitting the first digital surface representation to an appropriate fabrication tool, and using computer-aided manufacturing (CAM) software to translate the first digital surface representation into tooling motions, speeds, tool types (e.g., burr sizes and shapes for subtractive methods), and the like, to form the desired outer shape of the desired dental appliance, based on the first digital surface representation. The resulting preparation that includes only a portion (e.g., the desired outer shape) of the desired dental appliance can be referred to as a first "article," "preparation," or "intermediate."

The desired outer shape can be obtained using additive methods (e.g., building up material, such as by three-dimensional ("3D") printing, rapid-prototyping, selective laser sintering, stereolithography, other suitable additive methods, or a combination thereof); subtractive methods (e.g., machining from a mill block); or a combination thereof. For example, a mill block can be milled using a LAVA™ computer-integrated manufacturing system from 3M ESPE AG (Seefeld, Germany). In some embodiments, full chairside systems can be employed that include a scanner, software, and one or more mills, such as the Cerec System available from Sirona (Germany) and the E4D System available from D4D (Richardson, Tex.).

In embodiments in which the first article having the desired outer shape is prepared according to a subtractive process, such as milling, the first article can remain attached to a mandrel or frame (e.g., by a sprue) to facilitate indexing and registering the first article in the fabrication tool for later removing a portion (i.e., an inner portion) of the first article and forming the desired inner shape. In some embodiments (e.g., a "chairside" process, or a "single-appointment" or "same day" process), the entire outer layer can be formed in the same tool (e.g., mill), and the first article can simply remain mounted in the fabrication tool after step (ii), and the cavity can then be formed in the first article (i.e., in step (iii)). In some embodiments, the first article can be considered to include the sprue, or to be coupled to the sprue. In some embodiments, at the completion of step (ii), the inner structures, thickness, and the like, of the outer layer may not yet be known, and the first article can remain relatively "block-like" and oversized.

In some embodiments, the first article can be polished, for example, using a hand tool.

For layered, biomimetic and/or multi-chromatic dental appliances, such as dental restorations, the first material (e.g., the mill block used in subtractive methods) can be relatively hard and/or translucent relative to the second material, for example, to simulate an enamel layer.

In some embodiments, the first material can be formed of a polymeric material, a composite polymeric material, a glass-ceramic, or a combination thereof. For example, when subtractive methods are employed, the mill block from which the desired outer shape is milled can be formed of a polymeric material, a composite polymeric material, a glass-ceramic material, or a combination thereof. Such composites and glass-ceramics can both be milled in a timeframe that would allow the method to be performed "chairside," or in a "single-appointment" or "same day" process.

Polymeric materials (e.g., thermoplastics, such as polymethyl methacrylate, polycarbonate, etc., or combinations thereof; or thermosets, such as epoxies, polyurethanes, etc., or combinations thereof), or composite polymeric materials (i.e., filled polymeric materials, sometimes referred to herein as simply "polymeric composites" or "composites") can be used to form the dental appliance. Because of the material properties of polymeric materials, such materials can be used when all of the steps (i)-(viii) will be performed chairside. In such cases, a polymeric mill blank (e.g., a composite polymeric mill blank) can be provided, which can be attached to a mandrel, and which can be machined by any suitable machining equipment. Composites can include polymeric material filled with fillers, such as inorganic fillers (e.g., silica, zirconia, cluster fillers, other suitable inorganic fillers, or combinations thereof).

Examples of suitable polymeric or composite polymeric materials (i.e., filled polymeric materials) that can be employed include, but are not limited to, Paradigm MZ100 (3M ESPE), Vita CAD Temp Block (Vita Zahnfabrik, Germany), Telio CAD Block (Ivoclar, Liechtenstein), other suitable composite materials, or combinations thereof.

Glass-ceramic materials can generally be harder than polymeric materials, and at least partly because of the material properties of glass-ceramics, machining of the glass-ceramic may be more time-consuming. Still, it is conceivable that all of steps (i)-(viii) can be performed chairside when glass-ceramics are employed.

Examples of suitable glass-ceramic materials that can be employed include, but are not limited to, Vita Mark II (available from Vita Zahnfabrik, Germany), Empress CAD (available from Ivoclar Vivadent, Lichtenstein), Paradigm C (available from 3M ESPE, Seefeld, Germany), E-Max CAD (Ivoclar Vivadent), other suitable glass-ceramic materials, or combinations thereof.

Step (iii): Removing an Inner Portion of the First Article to Form an Outer Layer of the Dental Appliance Step (iii), "removing an inner portion of the first article to form an outer layer of the dental appliance comprising a cavity dimensioned to accommodate an inner layer," can also sometimes be referred to as milling an internal cutback of the first article. This step in the workflow can generally include transmitting information regarding the desired contours and outer layer thickness (which can be uniform or can vary at different locations on the appliance, as described above) to a fabrication tool via CAM software that can translate the data into tooling motions, speeds, tool types, etc. As mentioned above, such information can form a portion of, or be included in, the first digital surface representation. In some embodiments, however, such information can be provided to the fabrication tool separately from the first digital surface representation. For example, in some embodiments, the additional information can be a "second digital surface representation" that needs to be merged and reconciled with the first digital surface representation to form a first three-dimensional digital representation comprising all of the information regarding the outer layer. In such embodiments, the second digital surface representation described above as being acquired in step (vi) can be referred to as a "third digital surface representation," which can be merged (and registered) with the first three-dimensional digital representation to form a second three-dimensional digital representation that includes the details of the outer layer and the inner layer, including the desired outer shape of the dental appliance, as well as the desired inner shape of the dental appliance.

In some embodiments, removing a portion (e.g., an inner portion) of the first article can include removing a substantial portion of the first article, such that the resulting product is in the form of a relatively thin shell that can form the outermost portion of the desired dental appliance. For example, in some embodiments, "removing a substantial portion" of the first article can include removing more than 40% by volume (i.e., 40 vol %) of the first article, in some embodiments, more than 50% by volume, in some embodiments, more than 60% by volume, and in some embodiments, more than 75% by volume. Removing a substantial portion of the first article can also be defined by whether a substantially different second article was formed when a portion of the first article was removed and the resulting cavity was filled with a second material (the process for which is described in greater detail below). In some embodiments, e.g., with respect to a biomimetic dental appliance, a "substantially different" second article can generally refer to a second article that has a statistically significantly different material property, as compared to the first article (e.g., before any portion was removed), when tested according to standard testing methods for a particular material property of interest. In addition, in some embodiments, e.g., with respect to a multi-chromatic dental appliance, a "substantially different" second article can generally refer to a second article that is visually distinguishable (e.g., by the naked human eye) from the first article (e.g., before any portion was removed).

In some embodiments, this step can be performed by (a) inserting the first article into the same type of machine in which the first article was prepared (i.e., accommodating the same mandrel and having compatibility with the same data files), if the first article was prepared by the same method and prepared at a different location, in a different machine; (b) inserting the first article into the same machine (e.g., if the first article was formed at the same location—either at the dentist's office, or in another location); or (c) forming the cavity of the desired outer layer in the first article that is still residing in the machine in which the outer shape was formed (e.g., if the entire process is chairside and the first article was never removed from the machine in which the outer shape was formed).

The fabrication tool can then subtractively form the outer layer by forming a cavity in the first article that will eventually be filled with a second material that has a different material property than the first material of which the first article is formed. The second material can be formed of any of the polymeric materials, composite polymeric materials, and/or glass-ceramic materials described above.

In some embodiments, steps (ii) and (iii) above can be done simultaneously. For example, steps (ii) and (iii) can be performed simultaneously in embodiments in which the first digital surface representation includes all of the information necessary to form the complete outer layer, which can include, for example, the desired (e.g., final) outer shape of the dental appliance, along with the desired internal cavity shape (e.g., any internal mammelon structure(s)), the thickness of the outer layer, etc.

Step (iv): Forming a Second Article by Filling the Cavity of the First Article with a Second Material Adapted to Form the Inner Layer The outer layer formed in steps (ii) and (iii) having a desired outer shape (i.e., surface) and a cavity having a desired inner shape (e.g., including any desired mammelon structure, or having a nonspecific surface such that the outer layer has a generally uniform thickness) can then be filled with a second material in step (iv) to form a second article. That is, the interior cavity of the first article can be filled with a second material to form a second article having the desired outer shape, and the desired outer layer. The second article also includes an inner layer having a desired outer shape, which can be the desired inner cavity shape of the outer layer, or which can be sized to accommodate any intermediate layers, or a cement between the two layers. The inner layer will later be further processed to include an overall desired inner shape of the dental appliance. At this stage, however, the second article generally only includes the desired outer shape of the inner layer, and does not yet include the desired inner shape of the dental appliance.

In some embodiments, the method of the present disclosure can stop after step (iv), such that an exemplary method of the present disclosure can include steps (i)-(iv) only, the resulting product being a biomimetic (and, optionally, multi-chromatic), multi-layer intermediate dental appliance capable of being further processed, as desired, depending on specific patient circumstances. Such a resulting intermediate can include or be coupled to a mandrel or frame (e.g., by a sprue) to facilitate downstream processing.

In embodiments in which the second article having the desired outer shape is prepared according to a subtractive process, such as milling, the second article can remain attached to a mandrel or frame (e.g., by a sprue) to facilitate indexing and registering the second article in the fabrication tool for later forming the desired inner shape (e.g., for accommodating a tooth stump, an implant, an implant abutment, healing cap, or the like, or combinations thereof). In some embodiments (e.g., a "chairside" process, or a "single-appointment" or "same day" process), the second article can simply remain mounted in the fabrication tool, and the inner shape can be formed in the same tool in which the outer shape was formed. The second article can either be considered to include the sprue, or to be coupled to the sprue. At this point in time, the lower portion of the second article (e.g., subgingival portion) may not yet be known and can remain relatively "block-like" and oversized, to be finalized later in the process. It should be noted that the term "lower" is relative and depends on the orientation of the second article.

As mentioned above, the second material can be formed of any of the polymeric materials, composite polymeric materials, and/or glass-ceramic materials described above, and can include a different material property than the first material. For example, in some embodiments, the second material can include a flowable dental restoration polymeric material or paste, which can be cured. As a result, in embodiments employing a polymeric material, such as a composite, the filling step can also include a curing step.

Such a curing step can be done by photocuring (e.g., employing electromagnetic radiation, such as UV or visible radiation), chemical curing, and/or thermal curing. In some cases, step (iv) includes multiple filling and curing steps, such that the second material can be positioned in the cavity of the first article layer-by-layer (e.g., employing thinner layers) to compensate for composite shrinkage and to allow curing radiation to penetrate the composite (e.g., if a photocurable formulation is employed for the second material).

Examples of suitable composites for the second material can further include Filtek Supreme Flowable or Filtek Ultra, both of which are available from 3M ESPE.

In some embodiments, the second material can be formed of a polymeric composite which has been pre-cured and milled, e.g. from a mill blank, to fit within the cavity of the outer layer. This material would then be inserted and cemented to the first article. If this technique is used, the outer layer may not include undercuts that would prevent complete insertion of the polymeric composite inner layer.

As a result, in the methods of the present disclosure, the second material (which forms a layer of the dental appliance and which generally does not include any cement or adhesive used to couple the dental appliance to a dental object and/or to couple together layers of the dental appliance) can be positioned in the cavity of the outer layer, and then hardened (e.g., by curing) to form the second article, which can be further processed (e.g., subtractively, such as by machining) to form the desired inner shape of the dental appliance to accommodate a dental object. Alternatively, the second material can be hardened and shaped (e.g., by machining, such as milling) prior to being positioned in the cavity of the outer layer. However, a cement (or other bonding material or layer) that is pressed into place between the second material and the dental object, or between the first and second materials would not generally fall within the scope of creating a multi-chromatic or biomimetic dental appliance.

In some embodiments, the second material can be formed of a glass-ceramic material. In such embodiments, the glass-ceramic inner layer precursor can be formed according to similar methods used to form the outer shape of the first article. The outer shape of the inner layer can correspond directly to the desired inner cavity shape of the outer layer, or it can be sized to accommodate any intermediate layers, or a cement or adhesive. The inner layer can then be positioned in the cavity of the first article and adhered (e.g., via a cement or adhesive) or otherwise affixed in place to form the second article.

Furthermore, in embodiments employing a pre-formed (e.g., rigid, solid, etc.) inner layer (e.g., formed of a cured composite or a glass-ceramic), the cavity of the outer layer may include no undercuts that might prevent complete insertion of the inner layer. For example, the cavity can include a substantially uniform shape, or even a shape that tapers to a narrower shape toward the occlusal surface to facilitate coupling a pre-formed inner layer into the outer layer to form the second article. Alternatively, in some embodiments, the glass-ceramic inner layer can be formed to be slightly smaller than the cavity of the outer layer, which can allow the glass-ceramic inner layer to be pushed into a layer of uncured flowable polymeric material (e.g., a composite polymeric material), followed by a curing step to cure the polymeric material sandwiched between the outer layer and the inner layer.

As a result, methods of the present disclosure can be used to form multi-layer, biomimetic dental appliances, in which the different layers have different structural or material properties (i.e., different functions). In addition, the different layers can optionally also provide a multi-chromatic dental appliance where the different layers have different optical properties, such as different shades, different levels of transparency/translucency/opacity, etc. If the outer layer of the resulting dental appliance (i.e., formed of the first material) can be formed of a polymeric material or a glass-ceramic, and the inner layer (i.e., formed of the second material) can be formed of a polymeric or a glass-ceramic, but the layers need to have different material properties, then the following combinations are possible:

(a) an outer layer formed of a polymeric (e.g., a composite polymeric) material (such as Paradigm MZ100 (3M ESPE)), and an inner layer formed of a polymeric (e.g., a composite polymeric) material (such as Filtek Supreme Plus Flowable (3M ESPE)), where the outer polymeric material has different material properties than that of the inner polymeric material;

(b) an outer layer formed of a polymeric (e.g., a composite polymeric) material, and an inner layer formed of a glass-ceramic material;

(c) an outer layer formed of a glass-ceramic material, and an inner layer formed of a polymeric (e.g., a composite polymeric) material; and (d) an outer layer formed of a glass-ceramic material (such as Vita Mark II feldspathic porcelain (Vita)), and an inner layer formed of a glass-ceramic material (such as Paradigm C leucite reinforced ceramic (3M ESPE)), wherein the outer glass-ceramic material has different material properties than that of the inner glass-ceramic material.

All of the above combinations can be performed "chairside" or "same day." Of the above possible material combinations, combinations (b) and (c), and particularly, combination (c), may provide particular advantages, for example, in creating biomimetic dental appliances.

In some embodiments, the preceding steps (i.e., at least one of steps (i)-(iv) of the method described above) can be performed "off-site" and prior to the patient's visit during which the remaining steps occur. For example, in the situation where the first digital surface representation is acquired, at least partially, from one or more tooth libraries (or the patient's file history), the first article can be formed in an "off-site" manufacturing or laboratory setting, based on the first digital surface representation. Then, when the patient comes to the dentist's office to receive his/her dental appliance (e.g., a crown), the remaining steps (iii)-(vii) or (iii)-(viii) can be performed, using the first article that was previously created. Alternatively, in some embodiments, steps (i)-(iv) can all be performed "off-site" and prior to the patient's visit. Then, when the patient comes to his/her appointment to receive his/her dental appliance, the remaining steps (v)-(vii) or (v)-(viii) can be performed, using the second article that was previously created. In such embodiments, at least some of the steps would be considered to be performed "chairside." However, in some embodiments, all of the steps (i)-(viii) can be performed during one patient visit to the dentist's office, in which case, the entire process would be considered to be "chairside." In some embodiments, whether the entire process is completed sequentially at one location or some of the steps are completed at a different time (and potentially, at a different location), can be determined at least partially by the materials used to form the dental appliance.

Step (v): Providing a Dental Object Having an Outer Shape Comprising the Negative of the Desired Inner Shape of the Dental Appliance Step (v) of the method, "providing a dental object having an outer shape comprising the negative (e.g., volumetric inverse) of the desired inner shape of the dental appliance," can include preparing a tooth by removing carious parts of the tooth to be restored, leaving behind a tooth stump to receive the dental appliance (e.g., a crown; in the case of bridges, more than one tooth stump and pontic sites may receive the dental appliance); providing or preparing an implant, e.g., by coupling an implant abutment which will receive the dental appliance to a previously implanted dental implant; providing a healing cap; providing other suitable dental objects; or combinations thereof.

Step (vi): Acquiring a Second Digital Surface Representation of the Outer Shape of the Dental Object Step (vi) of the method, "acquiring a second digital surface representation of the outer shape of the dental object," can include any of the above-described optical scanning steps to capture digital data files representative of the dental object and create a second digital surface representation (e.g., by using CAD/CAM software to convert the digital data files to a three-dimensional model).

In some embodiments, step (vi) can also include inverting the second digital surface representation from a positive-volume digital surface representation of the dental object to a negative-volume digital surface representation to be formed (e.g., subtractively) in the second article.

In some embodiments, step (vi) can further include marking the gingival margin (e.g., using the CAD/CAM software), which can be done manually by the dental practitioner (e.g., dentist, assistant, dental lab technician, etc.). The CAD/CAM software tools can be used to create a "boundary" for the finished dental appliance.

Step (vi) can also include merging the first and second digital surface representations (e.g., using CAD/CAM software) to register, align, orient, and/or superimpose the two three-dimensional models relative to one another. The first and second digital surface representations can be registered, for example, by triangulating the positions of the dental objected (e.g., the tooth stump) within the digital surface representation of the first article (i.e., the dental appliance with only the desired outer shape but not yet the desired inner shape). This can be accomplished, for example, by aligning duplicate and unaltered points, such as digital surface representations of adjacent teeth or structures in the patient's mouth, from the first and second digital surface representations. In some embodiments, the second digital surface representation can itself include one or more indexing or reference points to assist in orienting or registering the second digital surface representation with the first digital surface representation when the two digital surface representations are merged.

In addition, in some embodiments, step (vi) can further include digitally designing the desired inner shape of the dental appliance to match (i.e., fit within) the already formed outer shape of the first article. Such designing can include any of the steps described above with respect to designing, refining or finalizing the first digital surface representation, and can further include translating a marked margin (if applicable) to a lower "boundary" of the finished dental appliance, and/or designing a gap or offset between the first digital surface representation and the second digital surface representation in the final merged three-dimensional digital representation to accommodate a layer of cement, for example.

The first and second digital surface representations can be stored at the stages of the process in which they are either provided or created, which can be at different times and at different locations. The first and second digital surface representations can then later be merged or meshed together to create a final three-dimensional model of the desired dental appliance.

In some embodiments, if the first digital surface representation is no longer available, another (e.g., a third) digital surface representation can be acquired by digital capturing (e.g., by optically scanning) the second article, which already includes the desired outer shape of the desired dental appliance. The third digital surface representation can then act as the first digital surface representation in the description above for the merging and registering the inner and outer digital surface representations of the desired dental appliance.

Step (vii): Forming the Desired Inner Shape

Step (vii), "forming the desired inner shape," can include subtractively forming the desired inner shape in the second article from the second digital surface representation. In some embodiments, the desired inner shape can be formed entirely in the inner layer of the second article; although, it is possible that the inner shape could extend at least slightly into the outer layer as well. In some embodiments, this step can be performed by (a) inserting the second article into the same type of machine in which the first article and/or outer layer were prepared (i.e., accommodating the same mandrel and having compatibility with the same data files), if the first article and/or outer layer was prepared by the same method and prepared at a different location, in a different machine; or (b) remounting the second article into the same machine (e.g., if the first article and/or outer layer was formed at the same location—either at the dentist's office, or in another location) after the second material has been positioned in the cavity of the outer layer.

The CAD/CAM software can direct the machine to subtractively form the desired inner shape in the second article, based on the steps performed in step (v), to form a dental appliance having a desired inner shape and a desired outer shape. In addition, the lower portion of the second article can simultaneously be machined to match the margin and to achieve a dental appliance of an appropriate size (e.g., height).

Step (viii): Place the Dental Appliance in the Patient's Mouth

Step (viii), "placing the dental appliance in the patient's mouth," can include cutting the dental appliance away from the sprue, any final firing steps (e.g., for crystallization, staining, and glazing), any final polishing steps (e.g., before or after placement in the patient's mouth), and/or any necessary coupling (e.g., adhesive, curing, etc.) steps for positioning the dental appliance in the patient's mouth (e.g., coupling to a tooth stump, implant abutment, or another suitable dental object).

The process of staining and/or glazing a dental appliance (e.g., a dental restoration) can include treating the outside of the appliance (e.g., a glass-ceramic restoration) to achieve a more natural appearance. Staining and glazing materials can be applied using a brush and then the dental appliance can be fired (e.g., at 750-1000° C.). In some embodiments, this process includes at least two steps: at least one for staining (which generally refers to shaded material), and at least one for glazing (which generally refers to translucent material). Staining can also be applied to composites using a polymeric stain, such as Sinfony Magic Shades, available from 3M ESPE.

The dental appliance can be affixed to the dental object (e.g., prepared tooth stump, implant abutment, etc.) with a dental cement, as known in the art. For example, the cavity (i.e., the cavity defined at least partially by the desired inner shape) of the dental appliance can be partially filled with a dental cement and then placed over the dental object, such that the base of the dental appliance contacts the necessary structures or tissues in the patient's mouth. Suitable dental cements are commercially available from 3M ESPE under the trade designation "RelyX Unicem Self Adhesive Universal Resin Cement."

In embodiments in which glass-ceramic materials are employed, the dental appliance having the desired inner shape and desired outer shape can be fired, which may produce a more durable, harder appliance. Such a firing step can be done relatively quickly, e.g., in some embodiments, such a firing step can be performed in less than 30 minutes.

As mentioned above, at least one of steps (i)-(iv) can be performed prior to the patient visit, and even at a different location. In embodiments in which the first article and/or the second article is formed "off-site," for example, at a dental laboratory, the machining equipment used in the dental laboratory can be compatible with the machining equipment used at the dentist's office, for completion of steps (v)-(vii), such that both devices use the same mandrel and mill blank. Such a mandrel can serve as an indexing feature to ensure that the inner shape is formed with the correct orientation, alignment, and relative positioning with respect to the outer shape. In such cases, the first article (and/or the second article) can be coupled to, or include, a sprue when it is provided to the dentist's office for the remaining steps. Conceivably, any remaining machining or finalizing (e.g., polishing, etc.) steps can also be performed off-site if the second digital surface representation is electronically transmitted to the dental laboratory. If the dental laboratory is geographically close to the dentist's office, this could conceivably still result in the entire process essentially being a chairside, or "single-appointment" or "same day" process.

As mentioned above, the dental appliance can include a variety of dental restorations, abutments, etc. Therefore, in some embodiments, the dental appliance can include a dental crown designed to be fit over a tooth stump or implant abutment. However, in some embodiments, the dental appliance can include a bridge. The methods of the present disclosure can be especially valuable for bridges, which may take a long time to mill, finish and polish the extensive outer surfaces as compared to a single unit crown. For example, a bridge can be designed and formed comprising three (or more) units, in which the two end units are each designed to fit over a tooth stump or implant abutment, with one or more solid pontics in between. In such embodiments, the outer shape can include the outer shape of the entire bridge (or the outer layer, including the desired outer shape and the desired inner cavity shape of the outer layer, can include the outer layer of the entire bridge), and the workflow can include one or more second digital surface representations, each corresponding to a dental object. By way of further example, one dental object could be a tooth stump, and one could be an implant abutment. The one or more inner shapes corresponding to the one or more second digital surface representations can be formed simultaneously or sequentially without departing from the spirit and scope of the present disclosure.

The method described above is broken into eight steps by way of simplicity and clarity. However, it should be understood that this breakdown of the methods and workflows of the present disclosure are by way of example only, and the method can instead include more or fewer steps than those outlined above. For example, step (vi) ("acquiring a second digital surface representation") is described above as including, in some embodiments, the steps of merging the first digital surface representation and the second digital surface representation and designing a three-dimension digital representation of the desired dental appliance. However, it should be understood, for example, that such steps can actually be thought of as additional steps in the methods of the present disclosure, and need not be considered to be a part of step (vi). Furthermore, such additional steps may actually be performed as a part of a different step, such as step (vii) ("forming the desired inner shape"), or may be combined in a different way. As a result, the present disclosure is not limited to the steps described above, or to the separation of steps described above. One exemplary method of the present disclosure will now be described in greater detail with respect to FIG. 1.

FIG. 1 illustrates a method 100 according to one embodiment of the present disclosure, for forming a dental restoration. The method 100 generally includes a first sequence 102 and a second sequence 104. The first sequence 102 and the second sequence 104 can include some temporal overlap, such that at least some of the steps in the first sequence 102 can occur while some of the steps in the second sequence 104 are being performed, or vice versa. In general, the first sequence 102 includes steps that can be performed on the patient, while the second sequence 104 generally refers to steps that include manipulating data, designing digital surface representations, and/or fabricating the dental restoration. Thus, the first sequence 102 generally takes place chairside. The second sequence 104 can also take place chairside (or in a back room or a portion of a dentist's office, which can also generally be referred to as "chairside" or "single-appointment" or "same day" because the steps are being performed while the patient is still at his/her appointment). As described above, in some embodiments, the second sequence 104 can take place partially chairside and partially remotely from the location of the patient. If the remote location is geographically near the location of the patient, however, the entire process can still occur while the patient is at his/her appointment, even if some of the software manipulation and/or fabrication steps are actually performed off-site, or remote from the location of the patient.

In the first sequence 102, a first step 106 of capturing the pre-op condition can be performed, which can include optically scanning a patient's soft tissue and dentition via one or more intraoral digital scans, or optically scanning a model (e.g., a standard model or a model of the patient's intraoral cavity), using the above-described digital workflow techniques. As shown in step 110, the digital data acquired from the scan can then be stored. The digital data files stored in step 110 can then be used, for example, at step 114, to design the outside contour of the restoration and to create a first digital surface representation (e.g., using CAD software). The inside contour of the desired outer layer can also be designed at step 114.

As further shown in FIG. 1, at step 116, the outside contour of the restoration can then be milled out of a first material using any standard dental milling fabrication tool. As discussed above, all of the steps 110, 114 and 116 can be performed during or prior to a tooth preparation step 120 (described below), and/or at a dental laboratory, remote from the dentist's office. The dental restoration formed in step 116 is generally referred to herein as a "first article," and the first article can be polished (e.g., while still being coupled to the mandrel). The first material can have certain structural and/or optical properties. For example, in some embodiments, the first material can be adapted to form an "enamel shell" that will be stronger and/or harder than an inner "dentin-like" layer. In addition, the first material can be enamel-shaded.

With continued reference to FIG. 1, at step 117, an outer layer of the restoration can be formed by milling a cavity in the first article. As described above, in some embodiments, the data regarding the specifics of the outer layer (e.g., internal mammelon structures, if applicable, thickness, etc.) can be included in the first digital surface representation. Because the first article is generally still coupled to a mandrel or frame (e.g., by a sprue), the cavity can be formed in the first article by remounting the first article in the same tool as that in which the outer shape was formed, or a different tool. The mandrel can facilitate registration of the second article in a fabrication tool, and can assist in indexing or registering the first article with respect to the fabrication tool when the cavity of the outer layer is formed in the first article (described below).

Alternatively, in embodiments in which the cavity will be formed in the same tool (e.g., mill) as the outer shape was formed, the first article can simply remain positioned in the fabrication tool (i.e., still coupled to or including the mandrel, sprue, etc.) after the outer shape is formed. Furthermore, in some embodiments, as described above, the cavity (e.g., internal surface) of the outer layer can be formed at the same time that the outer shape (e.g., external surface) is formed. In such embodiments, steps 116 and 117 can occur simultaneously as one step, and the resulting product can be a first article having the desired outer shape and the cavity.

The outer layer or "enamel shell" can optionally be stained and/or glazed to achieve a desired outer surface.

At step 118, a second article can then be formed by filling the cavity of the first article with a second material, namely, composite, and curing the composite. The composite is described with respect to the method 100 by way of example only; however, it should be understood that other materials (such as glass-ceramics) can be used instead, and the composite is described here and shown in FIG. 1 by way of example only. Furthermore, as described above, step 118 can actually include multiple layering steps, applying the second material in thin layers, and progressively curing each layer.

The second material will form the inner layer of the final dental restoration, and in the exemplary method 100, the second material has at least one different structural property (e.g., is softer, more shock-aborptive, and/or more resilient than the first material) and at least one different optical property (e.g., the second material can be darker than the first material) than the first material to form a biomimetic, multi-chromatic, multi-layer dental restoration. It can also be important that the outer layer and the inner layer (i.e., formed of the first material and the second material, respectively) have good interfacial bonding, for example, for structural integrity and sufficient biomimetics. In some embodiments of the method 100, step 118 can be the final step, and the resulting product can be an intermediate, biomimetic, multi-chromatic, multi-layer dental restoration, capable of being further processed as needed. Such a resulting intermediate can include or be coupled to a mandrel or frame (e.g., by a sprue) to facilitate downstream processing.

While steps 110, 114, 116, 117 and 118 are being performed, other actions can be taking place at the location of the patient. Alternatively, the following steps can occur after steps 110, 114, 116, 117 and 118 are complete. At step 120, a dental object can be formed, for example, by preparing a tooth to receive the dental restoration by removing carious dental tissue (e.g., hard tissue), by preparing an implant abutment (e.g., by coupling the implant abutment to an implant), according to known methods, or a combination thereof.

At step 126, a "post-prep" digital impression of the dental object can then be obtained, for example, by optically scanning the dental object.

Similar to step 114 above, the digital data files acquired at step 126 can be stored at step 130. Then, at step 134, the inside contours of the dental restoration can be designed, and the second digital surface representation can be formed. Also, at step 134, the first digital surface representation and the second digital surface representation can be merged and registered to form a complete three-dimensional digital representation of the desired dental restoration. In some embodiments, the second article can be considered to include, or be coupled to, a mandrel or holder that facilitates placement of the second article into a fabrication tool, such as a mill. The second article can further include, or be coupled to, a sprue that allows the second article to remain coupled to the mandrel, but from which the final dental restoration will be removed. The mandrel can facilitate registration of the second article in a fabrication tool, and can assist in indexing or registering the second article with respect to the fabrication tool when the inner shape of the dental restoration is formed in the second article (described below). In addition, in some embodiments, at step 134, any manipulation of the three-dimensional digital representation of the desired dental restoration can be performed, and margins can be designed into the model, along with any other necessary finalizing or data enhancement steps.

At step 136, the second article from step 118 can be milled to achieve the desired inside contour of the dental restoration to form the dental restoration having the desired outer shape (e.g., including margin(s)) and the desired inner shape.

Step 116, or the combination of steps 116, 117 and 118, can generally be referred to as the first fabrication step, or the "outer fabrication step," and step 136 can generally be referred to as the second fabrication step, or the "inner fabrication step," even though the inner fabrication step can include any finalizing that needs to be done with respect to the outer shape of the dental restoration. As a result, the fabrication steps for forming the inner shape of the dental restoration can be separated from and performed subsequently to steps for fabricating the outer shape of the dental restoration (with the exception of margins, or any additional finalizing of the outer shape, which can also be performed at step 136). As mentioned above, steps 116-118 need not be entirely completed before step 120 begins. Rather, steps 120 and 126 can occur while any of steps 110, 114, 116, 117 and 118 are still being performed.

Finally, as shown in FIG. 1, the method can include step 140, in which the completed restoration is placed in the patient's mouth, for example, using any cementation techniques known in the art.

In some embodiments, the method 100 can be described as including a first (or "outer") sequence 142 for creating the outer shape of the desired dental restoration, and a second (or "inner") sequence 144 for creating the inner shape of the desired dental restoration. In some embodiments, the outer sequence 142 can include steps 106, 110, 114, 116, 117 and 118, and the inner sequence 144 can include steps 120, 126, 130, 134 and 136. At least a portion of the outer sequence 142 can overlap temporally with the inner sequence 144, such that the inner sequence 144 can be initiated before the outer sequence 142 has been fully completed. Furthermore, as described above, the outer sequence 142 can be performed prior to the patient's visit, such that the second article is already prepared and ready for the inner sequence 144 to be completed when the patient arrives for his/her appointment. Alternatively, as described above, both the outer sequence 142 and the inner sequence 144 can be completed while the patient is at his/her appointment. In either scenario, the patient can leave the appointment with the desired dental restoration in place in his/her mouth.

Furthermore, in some embodiments, the outer sequence 142 can generally include a first sequence 146 for forming the first article, and a second sequence 148 for forming the second article. In the first sequence 146, the desired outer shape can be milled into a mill block of a desired first material having a desired structural and/or optical property to form the first article (i.e., step 116 in FIG. 1), and then a cavity can be milled out of the first article to form an outer layer of the dental restoration that includes the desired thickness, internal mammelon structure(s), translucency, etc. (i.e., step 117 in FIG. 1). In some embodiments, forming the cavity in the first article (i.e., step 117 in FIG. 1) can be considered to be a part of the first sequence 146, and in some embodiments, forming the cavity can be considered to be a part of the second sequence 146. The second sequence 148 can include forming the second article by filling the cavity in the first article with a second material having at least one structural and/or optical property that differs from the first material, such that the second article is biomimetic (and, optionally, multi-chromatic), and includes at least two layers.

As mentioned above, steps 117 and 118 can be repeated as many times as desired to form a second article having the desired number of layers, the desired level of biomimicry, the desired level of multi-chromaticity, the desired outer shape of the dental restoration, and the inner layer, in which the desired final inner shape of the dental restoration will be formed (i.e., step 136).

The method 100 is shown in FIG. 1 and described above for illustration purposes only, and it should be understood that the methods of the present disclosure are not limited to the specific embodiment shown in FIG. 1 and described above.

The following is a description of various embodiments of the present disclosure.

EMBODIMENTS

Embodiment 1 is a method of making a dental appliance, the method comprising:
provproviding a first digital surface representation of a desired outer shape of a dental appliance;
forming a first article of a first material having the desired outer shape based on the first digital surface representation;
removing an inner portion of the first article to form an outer layer of the dental appliance comprising a cavity dimensioned to accommodate an inner layer;
forming a second article by filling the cavity of the first article with a second material adapted to form the inner layer;
providing a dental object having an outer shape comprising the negative of a desired inner shape of the dental appliance;
acquiring a second digital surface representation of the outer shape of the dental object; and
subtractively forming the desired inner shape in the second article based on the second digital surface representation to form the dental appliance having the desired inner shape and the desired outer shape.

Embodiment 2 is a method of making a dental appliance, the method comprising:
providing a first digital surface representation of a desired outer shape of a dental appliance;
forming a first article of a first material having the desired outer shape based on the first digital surface representation;
removing an inner portion of the first article to form an outer layer of the dental appliance comprising a cavity dimensioned to accommodate an inner layer;
forming a second article by filling the cavity of the first article with a second material adapted to form the inner layer;
providing a dental object having an outer shape comprising the negative of a desired inner shape of the dental appliance;
acquiring a second digital surface representation of the outer shape of the dental object; and
subtractively forming the desired inner shape in the second article based on the second digital surface representation to form the dental appliance having the desired inner shape and the desired outer shape;
wherein at least one of providing a dental object and acquiring a second digital surface representation occurs during or after at least one of forming a first article, removing an inner portion of the first article, and forming a second article, and
wherein subtractively forming the desired inner shape occurs separately from and subsequently to forming a first article of a first material having the desired outer shape.

Embodiment 3 is the method of embodiment 1 or 2, further comprising repeating the removing an inner portion of the first article step and the forming a second article step as many times as desired to form a second article having a desired number of layers and comprising the inner layer.

Embodiment 4 is the method of any of embodiments 1-3, wherein the second material has at least one material property that is different from the first material, such that the dental appliance is biomimetic.

Embodiment 5 is the method of any of embodiments 4, wherein the second material further has at least one optical property that is different from the first material, such that the dental appliance is also multi-chromatic.

Embodiment 6 is the method of any of embodiments 1-5, wherein the first material is shaded to mimic an enamel layer, and wherein the second material is shaded to mimic a dentin layer.

Embodiment 7 is the method of any of embodiments 1-6, wherein the first material is formed of at least one of a polymeric composite and a glass-ceramic.

Embodiment 8 is the method of any of embodiments 1-7, wherein the second material is formed of at least one of a polymeric composite and a glass-ceramic, and wherein the second material includes at least one material or optical property that differs from the first material.

Embodiment 9 is the method of any of embodiments 1-8, wherein the first material is formed of a glass-ceramic material, and wherein the second material is formed of a polymeric composite material.

Embodiment 10 is the method of any of embodiments 1-9, wherein the dental object includes at least one of a tooth stump, an implant, an implant abutment, a healing cap, and a combination thereof.

Embodiment 11 is the method of any of embodiments 1-10, wherein forming a first article of a first material having the desired outer shape includes forming a first article by an additive process.

Embodiment 12 is the method of any of embodiments 1-10, wherein forming a first article of a first material having the desired outer shape includes forming a first article by a subtractive process.

Embodiment 13 is the method of any of embodiments 1-10 and 12, wherein forming a first article of a first material having the desired outer shape includes machining the desired outer shape from a mill block.

Embodiment 14 is the method of embodiment 13, wherein the mill block is formed of a glass-ceramic material.

Embodiment 15 is the method of any of embodiments 1-14, wherein subtractively forming the desired inner shape in the second article includes machining the desired inner shape.

Embodiment 16 is the method of any of embodiments 1-15, wherein subtractively forming the desired inner shape in the second article includes milling the desired inner shape.

Embodiment 17 is the method of any of embodiments 1-16, wherein acquiring a second digital surface representation of the outer shape of the dental object includes optically scanning the dental object.

Embodiment 18 is the method of any of embodiments 1-17, wherein at least two of forming a first article, removing an inner portion of the first article, and subtractively forming the desired inner shape in the second article are performed by the same fabrication tool.

Embodiment 19 is the method of any of embodiments 1-18, wherein at least two of forming a first article, removing an inner portion of the first article, and subtractively forming the desired inner shape in the second article occur at different locations from one another.

Embodiment 20 is the method of any of embodiments 1-19, further comprising acquiring a third digital surface representation of the second article.

Embodiment 21 is the method of any of embodiments 1-20, further comprising merging the first digital surface representation and the second digital surface representation to form a three-dimensional digital representation of the dental appliance.

Embodiment 22 is the method of any of embodiments 1-21, further comprising designing a three-dimensional digital representation of the dental appliance, wherein designing a three-dimensional digital representation includes merging the first digital surface representation and the second digital surface representation.

Embodiment 23 is the method of embodiment 22, wherein designing a three-dimensional digital representation of the dental appliance further includes orienting the first digital surface representation and the second digital surface representation with respect to one another.

Embodiment 24 is the method of embodiment 22, wherein designing a three-dimensional digital representation of the dental appliance further includes designing an offset between the first digital surface representation and the second digital surface representation to accommodate a cement or adhesive.

The following working example and prophetic example are intended to be illustrative of the present disclosure and not limiting.

EXAMPLES

Preparatory Example 1

Preparation of a Dental Blank Assembly Used in Example 1

Support (Mandrel) Fabrication

A commercially available metal mandrel designed to fit into a Cerec 3 milling unit (Sirona, Germany) was scanned with a LAVA™ ST Scanner (3M ESPE). The scan data were used to mill a LAVA™ Zirconia mill blank (3M ESPE) into the same shape as the metal mandrel, factoring in a shrinkage parameter such that the zirconia mandrel was the proper size after sintering. The milled zirconia was fully sintered per manufacturer's instructions in a LAVA™ Furnace 200 (3M ESPE), thus producing a fully sintered zirconia mandrel.

Mill Blank Attachment to the Mandrel

A feldspathic porcelain (Vita Mark II, Shade A3, Vident, Bad Sackingen, Germany) mill blank not having a mandrel was placed on a surface and a slurry of Vita VM9 porcelain (Vident) and LAVA™ Ceram Modeling Liquid (3M ESPE) was liberally painted on both the mill blank and the sintered zirconia mandrel. The mandrel was then pressed onto the blank using finger pressure and the assembly was carefully placed into a furnace (Vita Vacumat 4000T, Vident) and fired using the following temperature profile: 500 deg. C. for 6 min., then ramped at 25 deg. C./minute to 910 deg. C. and held at 910 deg. C. for 3 minutes. The vacuum was on during the heating and released when the temperature reached 910 deg. C. The fired assembly was slow cooled to 600 deg. C. and then cooled to room temperature, thus producing a mill blank attached to a mandrel (dental blank assembly).

Example 1

Chairside Preparation of an all-Ceramic Biomimetic Dental Restoration for a Patient Needing a Full Crown Using a Cerec 3 milling unit, an external shape in the form of an anterior prep was selected from the software library. Using the same software, an internal cavity was designed to have the same shape as the external surface, but being about 1 mm smaller, thus leaving a 1 mm exterior shell. The design of the outer layer of the restoration was then sent to the milling unit and milled from the dental blank assembly of Preparatory Example 1 to form the outer layer (which includes the desired outer shape and an internal cavity) of the restoration. A sprue was left, attaching the outer layer to the mandrel (thereby forming a "second assembly"). The outer layer and mandrel (i.e., the "second assembly") were removed from the mill.

The cavity formed inside the outer layer was scanned using an E4D system (D4D Technologies, Richardson, Tex.) and the digitized data was treated by the software as an inlay prep to create the design for the internal core having different physical properties from the outer layer. The design for the core was sent to the E4D milling unit and milled from an e.max CAD mill blank, shade HT A2 (Ivoclar Vivadent, Liechtenstein). The milled core was removed from the sprue.

The inside of the outer layer was coated with a slurry of LAVA™ DVS Fusion Porcelain, shade D3 (3M ESPE) and LAVA™ Ceram Modeling Liquid (3M ESPE) and the milled core was pressed into the coated interior. The assembled restoration, i.e., the "second article" still attached to the mandrel via the sprue (i.e., the "third assembly"), was fired in a Vita Vacuumat 4000T furnace using the following temperature profile: drying at 403° C. for 6 min., ramped at 30° C./min. to 850° C., held at 850° C. for 10 min., slow cooled to 680° C., then cooled to room temp, thus producing a restoration still attached to the mandrel (i.e., the fired third assembly) and having a lithium disilicate core within a feldspathic porcelain shell.

Further Prophetic Steps

While the milling procedure is occurring, the dentist prepares the patient's tooth, removing carious material and leaving a stump to which the restoration will be attached. A scan is taken of the preparation, digitized, the practitioner marks the margin, and the 3D model of the preparation is meshed with the 3D model of the restoration to determine a new internal surface for milling which is based on the preparation, margin and external shape of the restoration. The internal milling pathway is recalculated to sync with the previous milling pathway but the outer geometry is left as previously milled. In the new CAM milling pathway, the block geometry is calculated based on the shape generated in the previous steps (i.e., the desired inner shape is milled from the two-layer restoration attached to the mandrel).

The unfinished restoration is re-inserted into the mill, margins and cavity for the preparation are milled, the margins and cavity for the preparation are milled, and the finished restoration is removed from the sprue and polished, thus forming a completed restoration.

Example 2

Prophetic Example of a Chairside Preparation of a Biomimetic, Multi-Chromatic Dental Restoration for a Patient Needing a Full Crown A preoperative scan is taken of the tooth requiring restoration as well as the data from the adjacent and antagonist dentition using an intraoral scanning system such as the Lava Chairside Oral Scanner (C.O.S.; available from 3M ESPE). This data is then digitized and used to create a digital 3D model (i.e., a first digital surface representation) of the patient's teeth. The 3D model is then used to design the external surface (i.e., the desired outer shape) of the restoration. The shape and size of the existing tooth is desired for replication, so the external surface is cloned (i.e. not modified) using E4D design software (D4D Technologies, Richardson, Tex.). At this time, the gingival portion and margin of the restoration are left unfinished.

Using the same software, an internal cavity is designed to have the same shape as the external surface, but being 1 mm smaller, thus leaving a 1 mm exterior shell. The design of an outer layer of the restoration is now sent to a milling system (D4D) and milled from a Paradigm C glass-ceramic block (3M ESPE) to form a first article comprising the outer layer (which includes the desired outer shape and an internal cavity). A sprue is left, attaching the first article to the mandrel. The semi-finished restoration (i.e., the first article) is removed from the mill.

The hollow interior of the outer layer is first treated with an etching solution, such as Vita Cermics Etch (Vita Zahnfabrik, Germany), which is applied, allowed to stand for 30 seconds, and then rinsed off. The interior is next treated with Vitasil Silane Bonding Agent (Vita Zahnfabrik) per manufacturer's directions, then filled with dentin-shaded Filtek Supreme Plus Universal composite (3M ESPE) and photocured using an Elipar S10 curing lamp (3M ESPE) to form a second article comprising two layers of different material properties and different shades. The filled restoration (i.e., the second article) is now reinserted into the mill for the final milling step.

While the milling procedure is occurring, the dentist prepares the patient's tooth, removing carious material and leaving a stump to which the restoration will be attached.

A scan is taken of the preparation, digitized, the practitioner marks the margin, and the 3D model of the preparation is meshed with the 3D model of the restoration to determine a new internal surface for milling which is based on the preparation, margin and external shape of the restoration. The internal milling pathway is recalculated to sync with the previous milling pathway but the outer geometry is left as previously milled. In the new CAM milling pathway, the block geometry will be calculated based on the shape generated in the previous steps (i.e., the desired inner shape is milled from the second article).

The margins and cavity for the preparation are milled and the finished restoration is removed from the sprue and polished, thus forming a completed restoration ready for cementation to the preparation.

The embodiments described above and illustrated in the figures are presented by way of example only and are not intended as a limitation upon the concepts and principles of the present disclosure. As such, it will be appreciated by one having ordinary skill in the art that various changes in the workflow steps and their configuration are possible without departing from the spirit and scope of the present disclosure. Various features and aspects of the present disclosure are set forth in the following claims.

What is claimed is:

1. A method of making a dental appliance, the method comprising:
   providing a first digital surface representation of a desired outer shape of a dental appliance;
   forming a first article of a first material having the desired outer shape based on the first digital surface representation;
   removing an inner portion of the first article to form an outer layer of the dental appliance comprising a cavity dimensioned to accommodate an inner layer;
   forming a second article by filling the cavity of the first article with a second material adapted to form the inner layer;
   providing a dental object having an outer shape comprising the negative of a desired inner shape of the dental appliance;
   acquiring a second digital surface representation of the outer shape of the dental object; and
   subtractively forming the desired inner shape in the second article based on the second digital surface representation to form the dental appliance having the desired inner shape and the desired outer shape.

2. The method of claim 1,
   wherein at least one of providing a dental object and acquiring a second digital surface representation occurs during or after at least one of forming a first article, removing an inner portion of the first article, and forming a second article, and
   wherein subtractively forming the desired inner shape occurs separately from and subsequently to forming a first article of a first material having the desired outer shape.

3. The method of claim 1, further comprising repeating the removing an inner portion of the first article step and the forming a second article step as many times as desired to form a second article having a desired number of layers and comprising the inner layer.

4. The method of claim 1, wherein the second material has at least one material property that is different from the first material, such that the dental appliance is biomimetic.

5. The method of claim 4, wherein the second material further has at least one optical property that is different from the first material, such that the dental appliance is also multichromatic.

6. The method of claim 1, wherein the first material is shaded to mimic an enamel layer, and wherein the second material is shaded to mimic a dentin layer.

7. The method of claim 1, wherein the first material is formed of at least one of a polymeric composite and a glass-ceramic.

8. The method of claim 1, wherein the second material is formed of at least one of a polymeric composite and a glass-ceramic, and wherein the second material includes at least one material or optical property that differs from the first material.

9. The method of claim 1, wherein the first material is formed of a glass-ceramic material, and wherein the second material is formed of a polymeric composite material.

10. The method of claim 1, wherein the dental object includes at least one of a tooth stump, an implant, an implant abutment, a healing cap, and a combination thereof.

11. The method of claim 1, wherein forming a first article of a first material having the desired outer shape includes forming a first article by a subtractive process.

12. The method of claim 1, wherein subtractively forming the desired inner shape in the second article includes milling the desired inner shape.

13. The method of claim 1, wherein acquiring a second digital surface representation of the outer shape of the dental object includes optically scanning the dental object.

14. The method of claim 1, wherein at least two of forming a first article, removing an inner portion of the first article, and subtractively forming the desired inner shape in the second article are performed by the same fabrication tool.

15. The method of claim 1, wherein at least two of forming a first article, removing an inner portion of the first article, and subtractively forming the desired inner shape in the second article occur at different locations from one another.

* * * * *

UNITED STATES PATENT AND TRADEMARK OFFICE
CERTIFICATE OF CORRECTION

PATENT NO. : 8,973,269 B2  Page 1 of 1
APPLICATION NO. : 13/696638
DATED : March 10, 2015
INVENTOR(S) : Ryan Johnson et al.

It is certified that error appears in the above-identified patent and that said Letters Patent is hereby corrected as shown below:

On the Title Page, item 57, Column 2 (Abstract), Line 1 - delete "biometric" and insert -- biomimetic --, therefor.

In the Drawings

Sheet 1 (Reference No. 116) (Figure), Line 1 - delete "a a" and insert -- a --, therefor.

In the Specification

Column 28, Line 21 - delete "Vacuumat" and insert -- Vacumat --, therefor.

Column 29, Line 12 - delete "Cermics" and insert -- Ceramics --, therefor.

Signed and Sealed this
Eighteenth Day of August, 2015

Michelle K. Lee
*Director of the United States Patent and Trademark Office*